(12) United States Patent
Karasuda et al.

(10) Patent No.: US 9,328,063 B2
(45) Date of Patent: May 3, 2016

(54) METHOD FOR PRODUCING ACRYLONITRILE

(71) Applicant: Mitsubishi Rayon Co., Ltd., Chiyoda-ku (JP)

(72) Inventors: Takashi Karasuda, Yokohama (JP); Hirokazu Watanabe, Otake (JP); Motoo Yanagita, Yokohama (JP); Kazufumi Nishida, Otake (JP)

(73) Assignee: Mitsubishi Rayon Co., Ltd., Chiyoda-ku (JP)

( * ) Notice: Subject to any disclaimer, the term of this patent is extended or adjusted under 35 U.S.C. 154(b) by 0 days.

(21) Appl. No.: 14/381,360

(22) PCT Filed: Feb. 26, 2013

(86) PCT No.: PCT/JP2013/054944
§ 371 (c)(1),
(2) Date: Aug. 27, 2014

(87) PCT Pub. No.: WO2013/129385
PCT Pub. Date: Sep. 6, 2013

(65) Prior Publication Data
US 2015/0031907 A1   Jan. 29, 2015

(30) Foreign Application Priority Data

Feb. 29, 2012 (JP) ................................. 2012-042833

(51) Int. Cl.
*C07C 253/26* (2006.01)
*B01J 27/057* (2006.01)
*B01J 38/48* (2006.01)
*B01J 35/00* (2006.01)

(52) U.S. Cl.
CPC ........... *C07C 253/26* (2013.01); *B01J 27/0576* (2013.01); *B01J 35/0073* (2013.01); *B01J 38/485* (2013.01); *B01J 2523/00* (2013.01); *C07C 2521/08* (2013.01); *Y02P 20/584* (2015.11)

(58) Field of Classification Search
USPC .................................................. 558/322, 321
See application file for complete search history.

(56) References Cited

U.S. PATENT DOCUMENTS

| | | | |
|---|---|---|---|
| 3,194,278 A * | 7/1965 | Grob ...................... | D03D 45/50 139/247 |
| 3,988,359 A | 10/1976 | Saito et al. | |
| 4,409,122 A | 10/1983 | Kleuskens et al. | |
| 4,618,593 A | 10/1986 | Sasaki et al. | |
| 4,769,355 A * | 9/1988 | Glaeser ................. | B01J 23/002 502/202 |
| 4,983,752 A * | 1/1991 | Eichhorn .............. | C07C 253/26 558/322 |
| 5,132,269 A | 7/1992 | Sasaki et al. | |
| 5,160,721 A | 11/1992 | Sasaki et al. | |
| 6,036,880 A * | 3/2000 | Komada .................... | B01J 23/20 252/183.13 |
| 6,136,998 A * | 10/2000 | Sasaki ...................... | B01J 23/31 502/302 |
| 7,807,600 B2 * | 10/2010 | Watanabe et al. ............. | 502/255 |
| 8,034,736 B2 * | 10/2011 | Miyaki et al. ................. | 502/205 |
| 8,034,737 B2 * | 10/2011 | Watanabe et al. ............. | 502/212 |
| 8,350,075 B2 * | 1/2013 | Brazdil et al. ................ | 558/321 |
| 8,361,923 B2 * | 1/2013 | Kano et al. .................... | 502/311 |
| 8,586,786 B2 * | 11/2013 | Miura et al. ................... | 562/546 |
| 8,835,666 B2 * | 9/2014 | Brazdil et al. ................ | 558/324 |
| 2009/0234149 A1 | 9/2009 | Miyaki et al. | |
| 2015/0057463 A1 * | 2/2015 | Watanabe et al. ............. | 558/322 |
| 2015/0065744 A1 * | 3/2015 | Watanabe et al. ............. | 558/324 |

FOREIGN PATENT DOCUMENTS

| | | |
|---|---|---|
| CA | 1080203 A1 | 6/1980 |
| EP | 0 076 678 A2 | 4/1983 |
| JP | 38-019111 | 9/1963 |
| JP | 46-002804 | 1/1971 |
| JP | 47-018722 | 5/1972 |
| JP | 47-018723 | 5/1972 |
| JP | 47-019765 | 6/1972 |
| JP | 47-019766 | 6/1972 |
| JP | 47-019767 | 6/1972 |
| JP | 50-108219 | 8/1975 |
| JP | 52-125124 | 10/1977 |
| JP | 57-167736 | 10/1982 |
| JP | 57-187039 | 11/1982 |
| JP | 58-139745 | 8/1983 |

(Continued)

OTHER PUBLICATIONS

U.S. Appl. No. 14/381,047, filed Aug. 26, 2014, Watanabe, et al.

(Continued)

*Primary Examiner* — Nyeemah A Grazier
(74) *Attorney, Agent, or Firm* — Oblon, McClelland, Maier & Neustadt, L.L.P

(57) ABSTRACT

The invention relates to a method for producing acrylonitrile which includes a vapor phase catalytic ammoxidation process of performing vapor phase catalytic ammoxidation by bringing a source gas containing propylene, molecular oxygen, and ammonia into contact with a fluidized bed catalyst to obtain acrylonitrile. The method is characterized in that the fluidized bed catalyst consists of particles containing Fe, Sb, and Te, and the vapor phase catalytic ammoxidation process is performed while maintaining a B/A in the range of 2.0 to 5.0, where A denotes an atomic ratio of Te/Sb in a bulk composition of the fluidized bed catalyst and B denotes an atomic ratio of Te/Sb in a surface composition of the particles of the fluidized bed catalyst. According to the method for producing acrylonitrile of the invention, it is possible to stably maintain a high acrylonitrile yield over a long period of time.

11 Claims, No Drawings

(56) References Cited

FOREIGN PATENT DOCUMENTS

| | | |
|---|---|---|
| JP | 58-140056 | 8/1983 |
| JP | 59-139938 | 8/1984 |
| JP | 02-000152 | 1/1990 |
| JP | 02-000256 | 1/1990 |
| JP | 04-118051 | 4/1992 |
| JP | 2004-331533 | 11/2004 |
| JP | 2005-162707 A | 6/2005 |
| JP | 2005-254058 | 9/2005 |
| JP | 2009-220008 | 10/2009 |

OTHER PUBLICATIONS

International Search Report issued May 21, 2013 in PCT/JP2013/055014 (with English language translation).
Extended European Search Report issued Mar. 6, 2015 in Patent Application No. 13754387.2.
Robert K. Grasselli, "Selective Oxidation of Hydrocarbons Employing Tellurium Containing Heterogeneous Catalysts", Applied Catalysis, vol. 57, No. 2, XP 001208013, (Jan. 1, 1990), pp. 149-166.
International Search Report issued May 21, 2013 in PCT/JP2013/054944 filed Feb. 26, 2013.

* cited by examiner

METHOD FOR PRODUCING ACRYLONITRILE

This application is a National Stage of PCT/JP2013/054944 filed Feb. 26, 2013 and claims the benefit of JP 2012-042833 filed Feb. 29, 2012.

TECHNICAL FIELD

The present invention relates to a method for producing acrylonitrile by vapor phase catalytic ammoxidation of propylene by molecular oxygen and ammonia.

This application claims priority based on Japanese Patent Application No. 2012-042833 filed on Feb. 29, 2012, the entire contents of which are incorporated herein by reference.

BACKGROUND ART

A method is widely known in which acrylonitrile is produced by a vapor phase catalytic ammoxidation reaction using propylene, ammonia, and molecular oxygen (oxygen-containing gas) as a starting material in a fluidized reactor. In particular, a composite oxide catalyst containing iron and antimony is useful in the ammoxidation reaction and industrially widely used.

Hitherto, a large number of researches have been made on the composite oxide catalyst containing iron and antimony and thus various catalysts have been proposed.

For example, a composite oxide catalyst with at least one kind of element selected from the group consisting of iron, antimony, cobalt, and nickel is disclosed in Patent Document 1.

In addition, a composite oxide catalyst containing iron, antimony, tellurium, and further vanadium, molybdenum, tungsten, or the like is disclosed in Patent Documents 2 to 8. Moreover, a method for producing a catalyst containing these iron and antimony is disclosed in Patent Documents 9 to 11.

Furthermore, several proposals have also been made for the method for producing acrylonitrile which can suppress the time course of the catalyst performance and thus maintain a high acrylonitrile yield over a long period of time.

For example, it is specified in Patent Document 12 that the selectivity of the desired product and the catalytic activity are improved by enriching tellurium to the catalyst with decreased performance resulted from the use in a reaction and heating at a high temperature of 900° C. or lower. In addition, it is disclosed that a high acrylonitrile yield is maintained by replacing the catalyst in the reactor with this tellurium enriched catalyst.

In addition, it is disclosed in Patent Document 13 that the selectivity of the desired product and the time dependent decrease in the catalytic activity are improved by adding a tellurium support, a tellurium compound, and a molybdenum compound into the reactor during the ammoxidation reaction using a tellurium-containing oxide catalyst.

CITATION LIST

Patent Document

Patent Document 1: JP 38-19111 B
Patent Document 2: JP 46-2804 B
Patent Document 3: JP 47-19765 B
Patent Document 4: JP 47-19766 B
Patent Document 5: JP 47-19767 B
Patent Document 6: JP 50-108219 A
Patent Document 7: JP 52-125124 A
Patent Document 8: JP 4-118051 A
Patent Document 9: JP 47-18722 B
Patent Document 10: JP 47-18723 B
Patent Document 11: JP 59-139938 B
Patent Document 12: JP 58-139745 A
Patent Document 13: JP 58-140056 A

DISCLOSURE OF THE INVENTION

Problem to be Solved by the Invention

However, the catalyst or the method for producing thereof disclosed in these prior arts and the method for producing acrylonitrile exhibit an effect of maintaining a high acrylonitrile yield to some extent but the effect is not always sufficient. Accordingly, it is desired a method for producing acrylonitrile at a higher yield.

The invention has been made in view of the above circumstances, and an object thereof is to provide a method for producing acrylonitrile capable of stably maintaining a high acrylonitrile yield over a long period of time.

Means for Solving Problem

An aspect of the method for producing acrylonitrile of the invention is a method for producing acrylonitrile by the vapor phase catalytic ammoxidation of propylene by molecular oxygen and ammonia in a fluidized bed reactor using a fluidized bed catalyst consisting of particles containing iron (Fe), antimony (Sb), and tellurium (Te). The method is characterized in that the vapor phase catalytic ammoxidation reaction is performed while maintaining a B/A during the vapor phase catalytic ammoxidation reaction in the range of 2.0 to 5.0, where A denotes an atomic ratio of Te/Sb in a bulk composition of the fluidized bed catalyst and B denotes an atomic ratio of Te/Sb in a surface composition of the particles.

In addition, it is preferable that the bulk composition of the fluidized bed catalyst is represented by the following Formula (1).

$$Fe_{10}Sb_aA_bTe_cD_dE_eO_x \cdot (SiO_2)_y \qquad (1)$$

In Formula (1), Fe, Sb, Te, O, and $SiO_2$ represent iron, antimony, tellurium, oxygen, and silica, respectively, A represents at least one kind of element selected from the group consisting of vanadium, molybdenum, and tungsten, D represents at least one kind of element selected from the group consisting of magnesium, calcium, strontium, barium, titanium, zirconium, niobium, chromium, manganese, cobalt, nickel, copper, silver, zinc, boron, aluminum, gallium, indium, thallium, germanium, tin, lead, phosphorus, arsenic, and bismuth, E represents at least one kind of element selected from the group consisting of lithium, sodium, potassium, rubidium, and cesium, and a, b, c, d, e, x, and y represent an atomic ratio and a is 3 to 100, b is 0.1 to 5, c is 0.1 to 10, d is 0 to 50, e is 0 to 5, y is 10 to 200, and x is a number of oxygen atom required to satisfy a valence of each of the components except silica.

The method for producing acrylonitrile of the invention has the following aspects.

<1> A method for producing acrylonitrile, the method including a vapor phase catalytic ammoxidation process of performing vapor phase catalytic ammoxidation by bringing a source gas containing propylene, molecular oxygen, and ammonia into contact with a fluidized bed catalyst to obtain acrylonitrile, in which the fluidized bed catalyst consists of particles containing Fe, Sb, and Te, and the vapor phase catalytic ammoxidation process is performed while maintaining a B/A in the range of 2.0 to 5.0, where A denotes an atomic ratio of Te/Sb in a bulk composition of the fluidized bed catalyst and B denotes an atomic ratio of Te/Sb in a surface composition of the particles of the fluidized bed catalyst;

<2> The method for producing acrylonitrile according to <1>, in which the bulk composition of the fluidized bed catalyst is represented by the following Formula (1);

$$Fe_{10}Sb_aA_bTe_cD_dE_eO_x.(SiO_2)_y \quad (1)$$

in Formula (1), Fe, Sb, Te, O, and $SiO_2$ represent iron, antimony, tellurium, oxygen, and silica, respectively, A represents at least one kind of element selected from the group consisting of vanadium, molybdenum, and tungsten, D represents at least one kind of element selected from the group consisting of magnesium, calcium, strontium, barium, titanium, zirconium, niobium, chromium, manganese, cobalt, nickel, copper, silver, zinc, boron, aluminum, gallium, indium, thallium, germanium, tin, lead, phosphorus, arsenic, and bismuth, E represents at least one kind of element selected from the group consisting of lithium, sodium, potassium, rubidium, and cesium, and a, b, c, d, e, x, and y represent an atomic ratio and a is 3 to 100, b is 0.1 to 5, c is 0.1 to 10, d is 0 to 50, e is 0 to 5, y is 10 to 200, and x is a number of oxygen atom required to satisfy a valence of each of the components except silica. However, b, d, and e represent a sum of an atomic ratio of each element in a case in which A, D, and E contain two or more kinds of elements.

Effect of the Invention

According to the method for producing acrylonitrile of the invention, it is possible to stably maintain a high acrylonitrile yield over a long period of time.

MODE(S) FOR CARRYING OUT THE INVENTION

Hereinafter, the invention will be described in detail.

An aspect of the invention is a method for producing acrylonitrile by the vapor phase catalytic ammoxidation of propylene by molecular oxygen and ammonia in a fluidized bed reactor using a fluidized bed catalyst consisting of particles containing iron (Fe), antimony (Sb), and tellurium (Te). The method is characterized in that the vapor phase catalytic ammoxidation reaction is performed while maintaining a B/A during the vapor phase catalytic ammoxidation reaction in the range of 2.0 to 5.0, where A denotes an atomic ratio of Te/Sb in a bulk composition of the fluidized bed catalyst and B denotes an atomic ratio of Te/Sb in a surface composition of the particles.

In addition, another aspect of the invention is a method for producing acrylonitrile including a vapor phase catalytic ammoxidation process of performing vapor phase catalytic ammoxidation by bringing a source gas containing propylene, molecular oxygen, and ammonia into contact with a fluidized bed catalyst to obtain acrylonitrile. The method is characterized in that the fluidized bed catalyst consists of particles containing Fe, Sb, and Te, and the vapor phase catalytic ammoxidation process is performed while maintaining a B/A in the range of 2.0 to 5.0, where A denotes an atomic ratio of Te/Sb in a bulk composition of the fluidized bed catalyst and B denotes an atomic ratio of Te/Sb in a surface composition of the particles of the fluidized bed catalyst.

In the method for producing acrylonitrile by the vapor phase catalytic ammoxidation reaction of propylene using a fluidized bed catalyst containing iron and antimony in a fluidized bed reactor, there is a case in which the acrylonitrile yield time dependently decreases. As a result of intensive investigations on the reason for this, the present inventors have found out that the time dependent decrease of the acrylonitrile yield is caused by the time-dependent change of the surface composition of the fluidized bed catalyst particles. From the result, it has been found out that the time dependent decrease in the acrylonitrile yield can be suppressed by maintaining the B/A during the vapor phase catalytic ammoxidation reaction in the range of 2.0 to 5.0, where A denotes an atomic ratio of Te/Sb in a bulk composition of the fluidized bed catalyst and B denotes an atomic ratio of Te/Sb in a surface composition of the particles of the fluidized bed catalyst, thereby the invention has been completed.

In other words, in the invention, it is possible to stably maintain a high acrylonitrile yield over a long period of time by performing the vapor phase catalytic ammoxidation reaction while maintaining the B/A (hereinafter, referred to as "B/A of the fluidized bed catalyst") in the vapor phase catalytic ammoxidation reaction process in the range of 2.0 to 5.0, where A denotes an atomic ratio of Te/Sb in a bulk composition of the fluidized bed catalyst and B denotes an atomic ratio of Te/Sb in a surface composition of the particles of the fluidized bed catalyst.

The lower limit of the B/A of the fluidized bed catalyst during the vapor phase catalytic ammoxidation reaction process is preferably 2.4 and the upper limit thereof is preferably 4.6.

In the invention, the B/A of the unreacted fluidized bed catalyst (that is, before the fluidized bed catalyst is utilized in the vapor phase catalytic ammoxidation reaction) is not particularly limited as long as the B/A of the fluidized bed catalyst during the vapor phase catalytic ammoxidation process can be maintained in the range of 2.0 to 5.0. The B/A of the unreacted fluidized bed catalyst is preferably 2.4 to 4.6. It is possible to maintain the favorable catalytic performance, that is, a high acrylonitrile yield when the B/A of the unreacted fluidized bed catalyst satisfies the condition described above.

Here, the bulk composition of the fluidized bed catalyst refers to the composition of the whole aggregates of the fluidized bed catalyst having at least several tens of mg. Specifically, the bulk composition refers to the composition of the bulk particles of the fluidized bed catalyst having a particle size of 1 to 200 μm and more preferably 5 to 150 μm. The method for measuring the atomic ratio A of Te/Sb in the bulk composition of the fluidized bed catalyst is not particularly limited, and the atomic ratio A can be confirmed by performing elemental analysis by a known method, for example, ICP (inductively coupled plasma) high-frequency atomic emission spectroscopy, XRF (X-ray fluorescence) analysis, or atomic absorption spectrophotometry. In the invention, for the sake of convenience, a calibration curve method using a standard sample with a known quantity by XRF analysis is employed. In other words, in the invention, the composition of the fluidized bed catalyst measured by such a measurement method is taken as the "atomic ratio A of Te/Sb in the bulk composition of the fluidized bed catalyst".

Meanwhile, the surface composition of the particles in the fluidized bed catalyst refers to the ratio of the elements constituting a least surface layer in each of the particles of the fluidized bed catalyst. Here, the least surface layer refers to the layer including from the particle surface to a depth of about several nm. Specifically, the least surface layer means a layer including from the outermost layer of each of the particles of the fluidized bed catalyst to the depth of 5 nm and more preferably a layer including from the outermost layer to the depth of 3 nm. In the invention, the atomic ratio B of Te/Sb in the surface composition described above of the particles in the fluidized bed catalyst means a value determined through the measurement by XPS (X-ray photoelectron spectroscopy).

The B/A of the fluidized bed catalyst during the vapor phase catalytic ammoxidation process is determined by taking out a part of the fluidized bed catalyst from the fluidized bed reactor during the vapor phase catalytic ammoxidation process and measuring the atomic ratio A of Te/Sb in the bulk composition of the fluidized bed catalyst and the atomic ratio B of Te/Sb in the surface composition of the particles in the fluidized bed catalyst by the methods described above, respectively.

The amount of by-products such as hydrocyanic acid produced increases and thus the acrylonitrile yield decreases in a case in which the B/A of the fluidized bed catalyst during the vapor phase catalytic ammoxidation reaction process is smaller than the lower limit value, that is, 2.0.

On the other hand, the amount of by-products such as carbon dioxide produced increases and thus the acrylonitrile yield decreases in a case in which the B/A of the fluidized bed catalyst during the vapor phase catalytic ammoxidation reaction process is greater than the upper limit value, that is, 5.0.

Meanwhile, the reaction may be continued as it is when the B/A of the fluidized bed catalyst is within the above range, but the B/A of the fluidized bed catalyst may be increased or decreased to the extent in which the B/A of the fluidized bed catalyst is not out of the range described above.

An aspect of the method for producing acrylonitrile of the invention is characterized in that the vapor phase catalytic ammoxidation process is performed while maintaining the B/A of the fluidized bed catalyst in the range of 2.0 to 5.0. In other words, in the method for producing acrylonitrile of the invention, the vapor phase catalytic ammoxidation reaction process preferably includes the step of maintaining the B/A of the fluidized bed catalyst in the range of 2.0 to 5.0. It is preferable to use a method to increase the B/A of the fluidized bed catalyst or a method to decrease the B/A of the fluidized bed catalyst in order to maintain the B/A of the fluidized bed catalyst in a specific range.

As the method to increase the B/A of the fluidized bed catalyst during the vapor phase catalytic ammoxidation reaction process, it is effective to use a method in which a compound containing a tellurium element, specifically, tellurium powder, telluric acid, or the like is added into the reactor, a method in which a catalyst having a high B/A of the fluidized bed catalyst such as a catalyst prepared by impregnating tellurium, or the like is added into the reactor, or the like. In addition, a method of replacing a part of the catalyst in the reactor with a catalyst having a high B/A of the fluidized bed catalyst is also effective.

On the other hand, as the method to decrease the B/A of the fluidized bed catalyst during the vapor phase catalytic ammoxidation reaction process, it is also effective to use a method in which a catalyst having a low B/A of the fluidized bed catalyst is added into the reactor or a technique of temporarily raising the reaction temperature in the reactor.

In addition, a method of replacing a part of the catalyst in the reactor with a catalyst having a low B/A of the fluidized bed catalyst is also effective.

In addition, tellurium has a property of easily being volatilized during the reaction compared with antimony. By utilizing this property, the B/A of the fluidized bed catalyst during the reaction may also be controlled such that the volatilization of tellurium is promoted (or reduced) by temporarily raising (or lowering) the reaction temperature.

The timing for adding the compound containing a tellurium element, the catalyst prepared by impregnating tellurium, or the catalyst having a B/A of the fluidized bed catalyst different from the catalyst in the reactor, which is described above, or the addition amount thereof is not particularly limited as long as the effect of the invention is exhibited by the addition timing or the addition amount, but the B/A of the fluidized bed catalyst during the reaction tends to decrease as the vapor phase catalytic ammoxidation reaction proceeds. Consequently, the addition timing or the addition amount is preferably set such that the B/A of the fluidized bed catalyst during the vapor phase catalytic ammoxidation reaction is in the range described above.

Meanwhile, the method to control the B/A of the fluidized bed catalyst during the reaction is not limited to the methods described above, but the control of the B/A of the fluidized bed catalyst can be carried out by an arbitrary known method.

In the method for producing acrylonitrile of the invention, the vapor phase catalytic ammoxidation process is performed using a catalytic layer prepared by filling a fluidized bed catalyst in a fluidized bed reactor and by passing a source gas containing propylene, molecular oxygen, and ammonia through the catalytic layer.

The source gas is not particularly limited as long as the effect of the invention is exhibited by the source gas, but the source gas preferably has a ratio of propylene/ammonia/oxygen in the range of 1/1.0 to 2.0/1.0 to 5.0 (molar ratio).

The supply source of molecular oxygen which is an oxygen source is not particularly limited as long as the effect of the invention is exhibited by the supply source of molecular oxygen, but air is preferably used.

The source gas may be diluted with an inert gas such as nitrogen or carbon dioxide or saturated hydrocarbon, or may also be used by mixing with pure oxygen to increase the oxygen concentration.

The reaction temperature of the vapor phase ammoxidation reaction is preferably 350 to 500° C. and the reaction pressure thereof is preferably within the range of the normal pressure (100 kPa) to 500 kPa. The contact time of the fluidized bed catalyst with the reaction gas is preferably 0.1 to 20 seconds.

The fluidized bed catalyst used in the invention is not particularly limited as long as the fluidized bed catalyst satisfies the requirements described above, consists of particles containing iron, antimony, and tellurium, and exhibits the effect of the present invention, but it is preferable that the bulk composition thereof be represented by the following Formula (1) in terms of obtaining a high acrylonitrile yield.

$$Fe_{10}Sb_aA_bTe_cD_dE_eO_x\cdot(SiO_2)_y \tag{1}$$

In Formula (1), Fe, Sb, Te, O, and $SiO_2$ represent iron, antimony, tellurium, oxygen, and silica, respectively, A represents at least one kind of element selected from the group consisting of vanadium, molybdenum, and tungsten, D represents at least one kind of element selected from the group consisting of magnesium, calcium, strontium, barium, titanium, zirconium, niobium, chromium, manganese, cobalt, nickel, copper, silver, zinc, boron, aluminum, gallium, indium, thallium, germanium, tin, lead, phosphorus, arsenic, and bismuth, E represents at least one kind of element selected from the group consisting of lithium, sodium, potassium, rubidium, and cesium, and a, b, c, d, e, x, and y represent an atomic ratio and a is 3 to 100, b is 0.1 to 5, c is 0.1 to 10, d is 0 to 50, e is 0 to 5, y is 10 to 200, and x is a number of oxygen atom required to satisfy a valence of each of the components except silica. However, c, d, e and f represent a sum of an atomic ratio of each element in a case in which A, D, E and G contain two or more kinds of elements.

The method for producing the fluidized bed catalyst used in the invention is not particularly limited as long as the effect of the present invention is exhibited by the method, and the method may only follow the method for producing a catalyst described in, for example, Patent Documents 1 to 13 described above. Specifically, it is possible to exemplify a method in which a solution or aqueous slurry containing the starting material of each of the elements constituting the fluidized bed catalyst is prepared, the solution or aqueous slurry thus obtained is dried, and then the dry product thus obtained is calcined. In other words, the method for producing the fluidized bed catalyst of invention is preferably a method for producing the fluidized bed catalyst which includes step (I) of preparing a solution or aqueous slurry by mixing the respective elements constituting the fluidized bed catalyst and step (II) of drying the solution or aqueous slurry obtained in step (I) above and then calcining the dry product thus obtained.

In step (I), the solution or aqueous slurry may contain all of the desired elements constituting the fluidized bed catalyst of the invention at the desired atomic ratio. In addition, a solution or aqueous slurry containing some of the elements constituting the fluidized bed catalyst may be prepared and then the rest elements may be added to the catalyst composition dried or calcined by a method such as impregnation.

The starting material of each of the elements constituting the fluidized bed catalyst are determined according to its purpose, application, or the like, and it is preferable to use an oxide, or a nitrate, a carbonate, an organic acid salt, a hydroxide, an ammonium salt, or the like which is able to be easily formed into an oxide by igniting, or a mixture thereof.

A solution or aqueous slurry is obtained by mixing these starting materials as solids or after preparing solutions thereof by dissolving in water, dilute nitric acid, or the like. In addition, the fluidized bed catalyst of the invention contains silica, and silica sol is preferably used as the silica.

Upon the pH adjustment of the solution or aqueous slurry, the pH adjustment may be performed by the addition of nitric acid, aqueous ammonia, or the like if necessary, or performed by a concentration treatment, or a heat treatment.

Step (II) is a step of drying the solution or aqueous slurry obtained in step (I) above and then calcining the dry product thus obtained. In step (II), it is preferable to obtain a spherical dry product (dry particles) as possible by drying the solution or slurry containing the elements constituting the fluidized bed catalyst. Usually, drying is performed by spray drying. It is possible to use a common dryer such as a rotary disk type or a nozzle type as a dryer. The conditions for drying can be appropriately adjusted in order to obtain a catalyst having the preferred particle size distribution as a fluidized bed catalyst.

The catalytic activity is exerted by calcining the dry particles thus obtained. The calcination temperature is preferably 300 to 1000° C. The catalytic activity is hardly exerted when the calcination temperature is lower than the lower limit value above, that is, 300° C. In contrast, the activity is likely to deteriorate or the acrylonitrile yield is likely to decrease when the calcination temperature is higher than the upper limit value above, that is, 1000° C. In other words, it is preferable that the calcination temperature be 300 to 1000° C. since the catalytic activity is easily exerted and the acrylonitrile yield hardly decreases.

The calcination time is preferably 0.5 hour or longer since the catalytic activity is difficult to be sufficiently exerted when the calcination time is too short. The upper limit thereof is not particularly limited but is usually 20 hours or shorter since the performance of the catalyst is not enhanced to more than a certain extent even though the calcination time is extended longer than the required time. In other words, the calcination time is preferably 0.5 to 20 hours.

The furnace used for calcination is not particularly limited, and it is possible to use a box furnace, a rotary kiln, a fluidized bed furnace, or the like. For the production of fluidized bed catalyst, it is preferable to use a rotary kiln or a fluidized bed furnace by which calcination is performed while fluidizing the particles, and a fluidized bed furnace is particularly preferable in terms that uniform calcination is possible. It is preferable to perform calcination by dividing into two or more times since the acrylonitrile yield or the physical properties of the catalyst such as particle strength is improved.

In order to set the bulk composition of the fluidized bed catalyst within the range of Formula (1) above, it is possible to appropriately select, for example, the amount of each of the catalyst starting materials added in step (I) of preparing the solution or aqueous slurry described above or the amount of the catalyst starting materials added at each step until the drying step (II) after the step of preparing the solution or aqueous slurry. In addition, in the step (II), the amount of the catalyst starting materials added by impregnation or the like may be appropriately selected in the case of producing the catalyst by a method of impregnating the catalyst after drying or the like.

The bulk composition of the fluidized bed catalyst can be confirmed by performing the elemental analysis by XRF (X-ray fluorescence) analysis method as described above. It is also possible to calculate the bulk composition from the charged amount of each of the starting materials used at the time of producing the catalyst in the case of not using a significantly highly volatile element.

According to the method for producing acrylonitrile of the invention described above, it is possible to suppress a time-dependent decrease in the acrylonitrile yield and to stably maintain a high acrylonitrile yield over a long period of time by performing the vapor phase catalytic ammoxidation reaction while maintaining the B/A of the fluidized bed catalyst during the reaction in the range of 2.0 to 5.0 in the vapor phase catalytic ammoxidation reaction process. Consequently, the method for producing acrylonitrile of the invention is an economically advantageous method.

EXAMPLES

Hereinafter, the embodiments and effects of the invention will be specifically described with reference to Examples, but the invention is not limited to the present Examples.

The method for producing the fluidized bed catalyst used in each Example is described below.

In addition, the method for the activity test of the fluidized bed catalyst, and the methods for measurement of bulk composition of the fluidized bed catalyst, the atomic ratio A of Te/Sb in the bulk composition and the atomic ratio B of Te/Sb in the surface composition of the particles of the fluidized bed catalyst are described below.

[Production of Fluidized Bed Catalyst]

<Fluidized Bed Catalyst 1>

First, 68.8 g of copper powder was dissolved in 2400 g of 63% by mass nitric acid. To this solution, 2300 g of pure water was added and heated to 60° C. and then 201.7 g of electrolytic iron powder and 64.5 g of tellurium powder were added thereto little by little and dissolved. After confirming the dissolution thereof, 105.0 g of nickel nitrate, 43.3 g of chromium nitrate, and 10.4 g of manganese nitrate were added to this solution in order and dissolved (liquid A).

Separately, a solution (liquid B) in which 37.7 g of ammonium paratungstate was dissolved in 700 g of pure water and a solution (liquid C) in which 31.9 g of ammonium paramolybdate was dissolved in 100 g of pure water were prepared, respectively.

Subsequently, 6508.0 g of 20% by mass colloidal silica, 1052.6 g of antimony trioxide powder, liquid B, and liquid C were added to liquid A in order while stirring so as to obtain an aqueous slurry.

An aqueous slurry obtained by adding 15% by mass aqueous ammonia to the aqueous slurry obtained above dropwise and adjusting the pH to 2.0 was subjected to a heat treatment at the boiling point thereof for 3 hours under reflux.

The aqueous slurry after the heat treatment was cooled to 80° C., and 20.8 g of 85% by mass phosphoric acid and 40.2 g of boric acid were added thereto in order.

The aqueous slurry thus obtained was spray dried by a spray dryer at a drying air temperature of 330° C. at the dryer inlet and 160° C. at the dryer outlet to obtain spherical dry particles. Subsequently, the dry particles thus obtained was calcined at 250° C. for 2 hours and at 400° C. for 2 hours, and finally fluidized bed calcined at 800° C. for 3 hours using a fluidized bed furnace so as to obtain fluidized bed catalyst 1.

The bulk composition of fluidized bed catalyst 1 thus obtained was as follows.

$$Fe_{10}Sb_{20}Mo_{0.5}W_{0.4}Te_{1.4}Cu_3Ni_1P_{0.5}B_{1.8}Cr_{0.3}Mn_{0.1}O_x(SiO_2)_{60}$$

Here, x is the number of oxygen atom required to satisfy the valence of each of the components above except silica. It should be noted that the bulk composition of fluidized bed catalyst 1 is presented in Table 1 as well but the description of oxygen and the number (x) of oxygen atom is not presented in Table 1.

<Fluidized Bed Catalyst 2>

To 150 g of pure water heated at 50° C., 51.0 g of ammonium paramolybdate, 253.4 g of tellurium powder, and 200 g of 35% aqueous hydrogen peroxide were added in order, dissolved, and then continuously stirred for 3 hours. The liquid amount was adjusted to 720 mL by adding pure water thereto so as to prepare liquid D.

To 3000 g of fluidized bed catalyst 1, liquid D was added little by little so as to obtain mixture impregnated with liquid D.

This mixture was calcined at 500° C. for 3 hours in a rotary calcining furnace so as to obtain fluidized bed catalyst 2.

The bulk composition of fluidized bed catalyst 2 thus obtained was as follows.

$$Fe_{10}Sb_{20}M_{1.3}W_{0.4}Te_{6.9}Cu_3Ni_1P_{0.5}B_{1.8}Cr_{0.3}Mn_{0.1}O_x(SiO_2)_{60}$$

Here, x is the number of oxygen atom required to satisfy the valence of each of the components above except silica. It should be noted that the bulk composition of fluidized bed catalyst 2 is presented in Table 1 as well but the description of oxygen and the number (x) of oxygen atom is not presented in Table 1.

<Fluidized Bed Catalyst 3>

To 150 g of pure water heated at 50° C., 3.65 g of potassium nitrate was added, dissolved, and then stirred for 30 minutes. The liquid amount was adjusted to 720 mL by adding pure water thereto so as to prepare liquid E.

To 3000 g of fluidized bed catalyst 1, liquid E was added little by little so as to obtain a mixture impregnated with liquid E.

This mixture was calcined at 500° C. for 3 hours in a rotary calcining furnace so as to obtain fluidized bed catalyst 3.

The bulk composition of fluidized bed catalyst 3 thus obtained was as follows.

$$Fe_{10}Sb_{20}Mo_{0.5}W_{0.4}Te_{1.4}Cu_3Ni_1P_{0.5}B_{1.8}Cr_{0.3}Mn_{0.1}K_{0.1}O_x(SiO_2)_{60}$$

Here, x is the number of oxygen atom required to satisfy the valence of each of the components above except silica. It should be noted that the bulk composition of fluidized bed catalyst 3 is presented in Table 1 as well but the description of oxygen and the number (x) of oxygen atom is not presented in Table 1.

<Fluidized Bed Catalyst 4>

In 2110 g of 63% by mass nitric acid, 48.7 g of copper powder was dissolved. To this solution, 2710 g of pure water was added and heated to 60° C., and then 213.9 g of electrolytic iron powder and 88.0 g of tellurium powder were added thereto little by little and dissolved. After confirming the dissolution thereof, 29.5 g of manganese nitrate, 55.7 g of nickel nitrate, and 1.3 g of lithium nitrate were added to this solution in order and dissolved (liquid F).

Separately, a solution (liquid G) in which 10.0 g of ammonium paratungstate was dissolved in 270 g of pure water and a solution (liquid H) in which 40.6 g of ammonium paramolybdate was dissolved in 30 g of pure water were prepared, respectively.

Subsequently, 5178.4 g of 20% by mass silica sol and 1395.9 g of antimony trioxide powder were added to liquid F while stirring, and then an aqueous slurry obtained by adding 15% by mass aqueous ammonia thereto dropwise and adjusting the pH to 1.8 was subjected to a heat treatment for 3 hours under reflux.

The aqueous slurry after the heat treatment was cooled to 80° C., and 4.4 g of 85% by mass phosphoric acid, liquid G, and liquid H were added thereto in order.

The aqueous slurry thus obtained was spray dried by a spray dryer at a drying air temperature of 330° C. at the dryer inlet and 160° C. at the dryer outlet to obtain spherical dry particles. Subsequently, the dry particles thus obtained was calcined at 250° C. for 2 hours and at 400° C. for 2 hours, and finally fluidized bed calcined at 810° C. for 3 hours using a fluidized bed furnace so as to obtain fluidized bed catalyst 4.

The bulk composition of fluidized bed catalyst 4 thus obtained was as follows.

$$Fe_{10}Sb_{25}Mo_{0.6}W_{0.1}Te_{1.0}Cu_2Ni_{0.5}Mg_{0.3}P_{0.1}Li_{0.05}O_x(SiO_2)_{45}$$

Here, x is the number of oxygen atom required to satisfy the valence of each of the components above except silica. It should be noted that the bulk composition of fluidized bed catalyst 4 is presented in Table 1 as well but the description of oxygen and the number (x) of oxygen atom is not presented in Table 1.

<Fluidized Bed Catalyst 5>

Fluidized bed catalyst 5 was obtained in the same production manner as in fluidized bed catalyst 4 except that the amount of tellurium powder used for the preparation of liquid F was changed from 88.0 g to 219.9 g in the preparation of fluidized bed catalyst 4.

The bulk composition of fluidized bed catalyst 5 thus obtained was as follows.

$$Fe_{10}Sb_{25}Mo_{0.6}W_{0.1}Te_{2.5}Cu_2Ni_{0.5}Mg_{0.3}P_{0.1}Li_{0.05}O_x(SiO_2)_{45}$$

Here, x is the number of oxygen atom required to satisfy the valence of each of the components above except silica. It should be noted that the bulk composition of fluidized bed catalyst 5 is presented in Table 1 as well but the description of oxygen and the number (x) of oxygen atom is not presented in Table 1.

TABLE 1

| | Composition of catalyst (atomic ratio) | | | | | | | | | | | | | |
|---|---|---|---|---|---|---|---|---|---|---|---|---|---|---|
| | Fe | Sb | A | | Te | D | | | | | | | E | SiO$_2$ |
| | | | Mo | W | | Cu | Ni | Mg | P | B | Cr | Mn | | |
| Fluidized bed catalyst 1 | 10 | 20 | Mo 0.5 | W 0.4 | 1.4 | Cu 3 | Ni 1 | | P 0.5 | B 1.8 | Cr 0.3 | Mn 0.1 | | 60 |
| Fluidized bed catalyst 2 | 10 | 20 | Mo 1.3 | W 0.4 | 6.9 | Cu 3 | Ni 1 | | P 0.5 | B 1.8 | Cr 0.3 | Mn 0.1 | | 60 |
| Fluidized bed catalyst 3 | 10 | 20 | Mo 0.5 | W 0.4 | 1.4 | Cu 3 | Ni 1 | | P 0.5 | B 1.8 | Cr 0.3 | Mn 0.1 | K 0.1 | 60 |
| Fluidized bed catalyst 4 | 10 | 25 | Mo 0.6 | W 0.1 | 1 | Cu 2 | Ni 0.5 | Mg 0.3 | P 0.1 | | | | Li 0.05 | 45 |
| Fluidized bed catalyst 5 | 10 | 25 | Mo 0.6 | W 0.1 | 2.5 | Cu 2 | Ni 0.5 | Mg 0.3 | P 0.1 | | | | Li 0.05 | 45 |

[Activity Test of Fluidized Bed Catalyst]

The acrylonitrile synthesis reaction by vapor phase catalytic ammoxidation reaction of propylene was performed using the fluidized bed catalyst thus obtained in the following manner.

A fluidized bed reactor having a catalyst flow section with an inner diameter of 55 mm and a height of 2000 mm was filled with the fluidized bed catalyst so as to have a contact time of 3.2 seconds. The contact time of the fluidized bed catalyst with the reaction gas was determined by the following Formula.

Contact time (s)=catalyst volume by apparent bulk density standard (mL)/amount of supplied source gas in terms of reaction condition (mL/sec)

Air was used as the oxygen source, and the source gas having a composition of propylene:ammonia:oxygen=1:1.1:2.3 (molar ratio) was fed into the catalytic layer at a gas linear velocity of 17 cm/s. The reaction pressure was 200 kPa and the reaction temperature was 460° C.

A gas chromatography was used to quantify the reaction product, and the analysis was performed one or more times for every 100 hours. At that time, the amount of the catalyst was appropriately adjusted such that the conversion ratio of propylene was 97.8 to 98.2%. Specifically, the amount of the catalyst was adjusted by adding the fresh catalyst in a case in which the conversion ratio of propylene was less than this range. In addition, the conversion ratio of propylene was adjusted by taking out the catalyst from the reactor in a case in which the conversion ratio of propylene was greater than this range.

The conversion ratio of propylene, the acrylonitrile yield, and the ammonia combustion rate were determined by the following Equations.

Conversion ratio of propylene (%)={(carbon mass of supplied propylene−carbon mass of unreacted propylene)/(carbon mass of supplied propylene)}×100

Acrylonitrile yield (%)={(carbon mass of produced acrylonitrile)/(carbon mass of supplied propylene)}×100

Ammonia combustion rate (%)={(nitrogen mass of supplied ammonia−nitrogen mass of unreacted ammonia−nitrogen mass of trapped nitrogen-containing organic compounds)/(nitrogen mass of supplied ammonia)}×100

[Measurement of Bulk Composition of Fluidized Bed Catalyst and Atomic Ratio A of Te/Sb in the Bulk Composition]

The measurement of the bulk composition of the fluidized bed catalyst and the atomic ratio A of Te/Sb in the bulk composition were performed using an X-ray fluorescence spectrometer ("ZSX-PrimusII" manufactured by Rigaku Corporation). The quantification of Te and Sb in the fluidized bed catalyst was performed by a calibration curve method using a standard sample with a known quantity.

[Measurement of Atomic Ratio B of Te/Sb in Particle Surface of Fluidized Bed Catalyst]

The measurement of the atomic ratio B of Te/Sb in the particle surface was performed using an X-ray photoelectron spectrometer ("ESCALAB220iXL" manufactured by VG Scienta) and Al-kα ray as the X-ray source.

The atomic ratio B of Te/Sb in the particle surface composition of the fluidized bed catalyst was determined according to the procedure in which firstly, the peak area intensity of Te3d5 and the peak area intensity of Sb3d3 were calculated with regard to the XPS spectrum obtained by the measurement, subsequently each of the peak area intensities was corrected by the device specific relative sensitivity factor, and then the ratio thereof was determined.

Example 1

The activity test and the analysis of the physical properties (XRF analysis measurement and XPS measurement) of the catalyst taken out from the reactor were performed in the following manner.

The acrylonitrile synthesis reaction by the vapor phase catalytic ammoxidation reaction was performed using fluidized bed catalyst 1. Meanwhile, the XRF analysis measurement and the XPS measurement were performed with regard to the unreacted catalyst, as a result, the B/A of the fluidized bed catalyst was 4.1.

The analysis of the reaction gas was performed in 100 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the XRF analysis measurement and the XPS measurement.

Subsequently, the reaction was continued, and the analysis of the reaction gas was performed in 300 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the XRF analysis measurement and the XPS measurement. In 325 hours from the start of the reaction, metal tellurium was added into the reactor in an amount corresponding to 0.2% of the mass of the catalyst in the reactor and then the reaction was continued.

The analysis of the reaction gas was performed in 500 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the XRF analysis measurement and the XPS measurement. In 525 hours from the start of the reaction, fluidized bed catalyst 2 was added into the reactor in an amount corresponding to 2% of the mass of the catalyst in the reactor and then the reaction was continued.

The analysis of the reaction gas was performed in 700 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the XRF analysis measurement and the XPS measurement. In 725 hours from the start of the reaction, fluidized bed catalyst 3 was added into the reactor in an amount corresponding to 5% of the mass of the catalyst in the reactor and then the reaction was continued.

The analysis of the reaction gas was performed in 1000 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the XRF analysis measurement and the XPS measurement.

The results of these are presented in Table 2.

Example 2

The acrylonitrile synthesis reaction by the vapor phase catalytic ammoxidation reaction was performed using the same fluidized bed catalyst 1 as in Example 1 in the following manner.

The operation was performed in the same manner as in Example 1 until 525 hours from the start of the reaction, and fluidized bed catalyst 2 was added into the reactor in an amount corresponding to 4% of the mass of catalyst in the reactor in 525 hours from the start of the reaction and then the reaction was continued. In addition, the operation was performed in the same manner as in Example 1 after this as well.

The analysis of the reaction gas was performed in 100, 300, 500, 700, and 1000 hours from the start of the reaction and thus the conversion ratio of propylene, the acrylonitrile yield, and the ammonia combustion rate were determined. In addition, about 5 g of the catalyst was taken out from the reactor immediately after each of the analyses of the reaction gas and then subjected to the XRF analysis measurement and the XPS measurement.

The results of these are presented in Table 2.

Example 3

The acrylonitrile synthesis reaction by the vapor phase catalytic ammoxidation reaction was performed using fluidized bed catalyst 4. Meanwhile, the XRF analysis measurement and the XPS measurement were performed with regard to the unreacted catalyst, as a result, the B/A of the fluidized bed catalyst was 3.0.

The analysis of the reaction gas was performed in 100 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the XRF analysis measurement and the XPS measurement.

Subsequently, the reaction was continued, and the analysis of the reaction gas was performed in 300 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the XRF analysis measurement and the XPS measurement. In 325 hours from the start of the reaction, the catalyst was taken out from the reactor in an amount corresponding to 10% of the mass of the catalyst in the reactor and fluidized bed catalyst 5 was added into the reactor in an amount equal to that of the catalyst taken out, and then the reaction was continued.

The analysis of the reaction gas was performed in 500 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the XRF analysis measurement and the XPS measurement. In 525 hours from the start of the reaction, ammonium molybdate was added into the reactor in an amount corresponding to 8% of the mass of the catalyst in the reactor and then the reaction was continued.

The analysis of the reaction gas was performed in 700 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the XRF analysis measurement and the XPS measurement. In 725 hours from the start of the reaction, fluidized bed catalyst 4 was added into the reactor in an amount corresponding to 2% of the mass of the catalyst in the reactor and then the reaction was continued.

The analysis of the reaction gas was performed in 1000 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the XRF analysis measurement and the XPS measurement.

The results of these are presented in Table 2.

Comparative Example 1

The same operation as in Example 3 was performed using the same fluidized bed catalyst 4 as in Example 3 except that fluidized bed catalyst 5 and ammonium molybdate were not added during the reaction.

The analysis of the reaction gas was performed in 100, 300, 500, 700, and 1000 hours from the start of the reaction and thus the conversion ratio of propylene, the acrylonitrile yield, and the ammonia combustion rate were determined. In addition, about 5 g of the catalyst was taken out from the reactor immediately after each of the analyses of the reaction gas and then subjected to the XRF analysis measurement and the XPS measurement.

The results of these are presented in Table 2.

Comparative Example 2

The acrylonitrile synthesis reaction by the vapor phase catalytic ammoxidation reaction was performed using the same fluidized bed catalyst 1 as in Example 1 in the following manner.

The analysis of the reaction gas was performed in 100 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the XRF analysis measurement and the XPS measurement. In 125 hours from the start of the reaction, the catalyst was taken out from the reactor in an amount corresponding to 10% of the mass of the catalyst in the reactor and fluidized bed catalyst 2 was added into the reactor in an amount equal to that of the catalyst taken out, and then the reaction was continued.

The analysis of the reaction gas was performed in 300 hours from the start of the reaction. In addition, about 5 g of the catalyst was taken out from the reactor immediately after the analysis of the reaction gas and then subjected to the XRF analysis measurement and the XPS measurement.

The results of these are presented in Table 2.

In addition, in the case of Comparative Example 2, the yield of acrylonitrile decreased during the vapor phase catalytic ammoxidation reaction when the B/A of the fluidized bed catalyst during the reaction was greater than 5.0.

From these results, the acrylonitrile yield when the B/A of the fluidized bed catalyst during the vapor phase catalytic ammoxidation process was in the range of 2.0 to 5.0 was higher than the yield when the B/A of the fluidized bed catalyst was out of the range above. It was confirmed that the relation of the B/A of the fluidized bed catalyst and the yield of acrylonitrile, namely, a decrease in the yield of acrylonitrile can be effectively suppressed when the B/A of the fluidized bed catalyst is within the above range.

Consequently, according to the invention, it is possible to suppress a time dependent decrease in the acrylonitrile yield and to stably maintain a high acrylonitrile yield over a long period of time by performing the vapor phase catalytic ammoxidation reaction while maintaining the B/A of the

TABLE 2

| | | | Results of Analysis | | | Activity Test | | |
|---|---|---|---|---|---|---|---|---|
| | Catalyst | Elapsed Time [hour] | A | B | B/A | Conversion ratio of propylene [%] | Acrylonitrile yield [%] | Ammonia combustion rate [%] |
| Example 1 | Fluidized bed catalyst 1 | 0 | 0.070 | 0.29 | 4.1 | — | — | — |
| | | 100 | 0.070 | 0.26 | 3.7 | 98.2 | 80.6 | 2.1 |
| | | 300 | 0.069 | 0.23 | 3.3 | 98.1 | 80.7 | 1.4 |
| | | 500 | 0.074 | 0.28 | 3.8 | 98.0 | 80.7 | 1.1 |
| | | 700 | 0.075 | 0.32 | 4.3 | 97.9 | 80.5 | 2.5 |
| | | 1000 | 0.073 | 0.30 | 4.1 | 98.0 | 80.6 | 1.0 |
| Example 2 | Fluidized bed catalyst 1 | 0 | 0.070 | 0.29 | 4.1 | — | — | — |
| | | 100 | 0.070 | 0.26 | 3.7 | 98.2 | 80.6 | 2.1 |
| | | 300 | 0.069 | 0.22 | 3.2 | 98.1 | 80.7 | 1.4 |
| | | 500 | 0.074 | 0.28 | 3.8 | 98.0 | 80.8 | 1.1 |
| | | 700 | 0.082 | 0.39 | 4.8 | 97.8 | 80.0 | 3.5 |
| | | 1000 | 0.080 | 0.36 | 4.5 | 98.2 | 80.7 | 1.3 |
| Example 3 | Fluidized bed catalyst 4 | 0 | 0.040 | 0.12 | 3.0 | — | — | — |
| | | 100 | 0.039 | 0.10 | 2.6 | 98.0 | 80.7 | 1.2 |
| | | 300 | 0.038 | 0.08 | 2.1 | 97.8 | 80.0 | 0.8 |
| | | 500 | 0.050 | 0.16 | 3.2 | 98.1 | 80.6 | 1.4 |
| | | 700 | 0.045 | 0.14 | 3.1 | 97.9 | 80.7 | 1.8 |
| | | 1000 | 0.044 | 0.13 | 3.0 | 98.0 | 80.6 | 1.6 |
| Comparative Example 1 | Fluidized bed catalyst 4 | 0 | 0.040 | 0.12 | 3.0 | — | — | — |
| | | 100 | 0.039 | 0.10 | 2.6 | 98.1 | 80.7 | 1.3 |
| | | 300 | 0.038 | 0.08 | 2.1 | 97.9 | 80.1 | 0.9 |
| | | 500 | 0.036 | 0.07 | 1.9 | 97.8 | 79.2 | 0.5 |
| | | 700 | 0.035 | 0.06 | 1.7 | 98.1 | 78.8 | 0.3 |
| | | 1000 | 0.033 | 0.05 | 1.5 | 97.9 | 78.2 | 0.2 |
| Comparative Example 2 | Fluidized bed catalyst 1 | 0 | 0.070 | 0.29 | 4.1 | — | — | — |
| | | 100 | 0.070 | 0.25 | 3.6 | 98.1 | 80.6 | 2.2 |
| | | 300 | 0.090 | 0.50 | 5.6 | 98.0 | 77.8 | 5.3 |

As can be seen from the results of Table 2, it was possible to produce acrylonitrile while maintaining a high acrylonitrile yield of 80% or more in the case of Examples 1 to 3 in which the vapor phase catalytic ammoxidation reaction was performed while maintaining the B/A of the fluidized bed catalyst during the vapor phase catalytic ammoxidation process in the range of 2.0 to 5.0. It was possible to produce acrylonitrile while maintaining a higher acrylonitrile yield of 80.5% or more particularly in the case of Example 1 in which the vapor phase catalytic ammoxidation reaction was performed while maintaining the B/A of the fluidized bed catalyst during the reaction in the range of 2.4 to 4.6.

On the other hand, in the case of Comparative Example 1, the yield of acrylonitrile decreased during the vapor phase catalytic ammoxidation reaction when the B/A of the fluidized bed catalyst during the reaction was smaller than 2.0.

fluidized bed catalyst during the vapor phase ammoxidation process in the range of 2.0 to 5.0.

The invention claimed is:

1. A method for producing acrylonitrile, the method comprising performing a vapor phase catalytic ammoxidation process by bringing a source gas containing propylene, molecular oxygen, and ammonia into contact with a fluidized bed catalyst to obtain acrylonitrile,
   wherein the fluidized bed catalyst comprises particles containing Fe, Sb, and Te, and
   the vapor phase catalytic ammoxidation process is performed while maintaining a B/A ratio in the range of 2.4 to 4.6, where A denotes an atomic ratio of Te/Sb in a bulk composition of the fluidized bed catalyst and B denotes an atomic ratio of Te/Sb in a surface composition of the particles of the fluidized bed catalyst.

2. The method for producing acrylonitrile according to claim 1, wherein the bulk composition of the fluidized bed catalyst is represented by the following Formula (1)

$$Fe_{10}Sb_aA_bTe_cD_dE_eO_x(SiO_2)_y \quad (1)$$

(wherein Fe, Sb, Te, O, and $SiO_2$ represent iron, antimony, tellurium, oxygen, and silica, respectively;

A represents at least one element selected from the group consisting of vanadium, molybdenum, and tungsten;

D represents at least one element selected from the group consisting of magnesium, calcium, strontium, barium, titanium, zirconium, niobium, chromium, manganese, cobalt, nickel, copper, silver, zinc, boron, aluminum, gallium, indium, thallium, germanium, tin, lead, phosphorus, arsenic, and bismuth;

E represents at least one element selected from the group consisting of lithium, sodium, potassium, rubidium, and cesium; and a, b, c, d, e, x, and y represent an atomic ratio and a is 3 to 100, b is 0.1 to 5, c is 0.1 to 10, d is 0 to 50, e is 0 to 5, y is 10 to 200, and x is a number of oxygen atom required to satisfy a valence of each of the components except silica provided that b, d, and e represent a sum of an atomic ratio of each element where A, D, and E contain two or more elements.

3. The method according to claim 1, wherein the fluidized bed catalyst consists of particles containing Fe, Sb, and Te.

4. The method according to claim 1, wherein the source gas has a molar ratio of propylene/ammonia/oxygen in the range of 1/1.0 to 2.0/1.0 to 5.0.

5. The method according to claim 1, wherein the vapor phase ammoxidation reaction is conducted at a temperature of 350 to 500° C, at a pressure of 100 kPa to 500 kPa, and the contact time of the fluidized bed catalyst with the reaction gas is 0.1 to 20 seconds.

6. The method according to claim 1, wherein the particles are from 1 to 200μm in size.

7. The method according to claim 1, wherein the particles are from 5 to 150 μm in size.

8. The method according to claim 2, wherein the source gas has a molar ratio of propylene/ammonia/oxygen in the range of 1/1.0 to 2.0/1.0 to 5.0.

9. The method according to claim 2, wherein the vapor phase ammoxidation reaction is conducted at a temperature of 350 to 500° C, at a pressure of 100 kPa to 500 kPa, and the contact time of the fluidized bed catalyst with the reaction gas is 0.1 to 20 seconds.

10. The method according to claim 2, wherein the particles are from 1 to 200 μm in size.

11. The method according to claim 2, wherein the particles are from 5 to 150 μm in size.

* * * * *